United States Patent [19]

Meeks et al.

[11] 4,187,285

[45] Feb. 5, 1980

[54] MICROAGGREGATED ALBUMIN

[75] Inventors: Marion Meeks, East Windsor; R. K. Narra, North Brunswick, both of N.J.

[73] Assignee: E. R. Squibb & Sons, Inc., Princeton, N.J.

[21] Appl. No.: 861,231

[22] Filed: Dec. 16, 1977

[51] Int. Cl.² ............. A61K 29/00; A61K 43/00; G01N 33/16

[52] U.S. Cl. ............................. 424/1; 252/316; 260/112 R; 260/122; 424/9

[58] Field of Search ............ 424/1, 9; 260/112 R, 260/122; 252/316

[56] References Cited

U.S. PATENT DOCUMENTS 3,872,226  3/1975  Haney et al. ................. 424/1

4,094,965  6/1978  Layne et al. ................. 424/1.5

OTHER PUBLICATIONS

Honda et al., J. of Nucl. Med., vol. 11, No. 10, 1970, pp. 580–585.

Primary Examiner—Benjamin R. Padgett
Assistant Examiner—Christine M. Nucker
Attorney, Agent, or Firm—Lawrence S. Levinson; Donald J. Barrack

[57] ABSTRACT

A composition suitable for labeling with technetium-99 m and subsequent use as an agent for the imaging of the reticuloendothelial system comprising microaggregated particles of denatured albumin having stannous ions bound thereto and being substantially free of buffer, and a process for preparing such a composition are disclosed herein.

6 Claims, No Drawings

MICROAGGREGATED ALBUMIN

BACKGROUND OF THE INVENTION

U.S. Pat. Nos. 3,872,226 and 3,863,004 disclose the preparation of macroaggregates denatured albumin having divalent tin bound thereto. A related disclosure can be found in U.S. Pat. No. 4,024,233. The macroaggregates referred to are suitable for tagging with technetium-99m, and when so tagged, can be used in perfusion lung scanning to obtain information about the pulmonary vasculature. The size of the macroaggregates must be of the order of about 5 to 100 microns so that when administered to a patient they will localize in his lungs.

U.S. Pat. No. 3,863,004 also discusses the labeling of denatured albumin microspheres with technetium sulfur colloid. It is stated, however, that the tagged microspheres tend to agglomerate, and that it is necessary to subject the agglomerated particles to an "appropriate technique" (ultrasonic treatment is suggested) to disperse them. U.S. Pat. No. 3,872,226 discloses the washing of the macroaggregates.

In addition to the above-described technetium-99m labeled macroaggregates of denatured albumin, the prior art also discloses the preparation of microaggregates of iodine-131 labeled denatured albumin (see Kutas et al., *International Journal of Applied Radiation and Isotopes*, 26:31 (1975)) and of microaggregates of technetium-99m labeled denatured albumin (see Yamada et al., *Journal of Nuclear Medicine*, 10(6):453 (1969) and Honda et al., *Journal of Nuclear Medicine*, 11(10):580 (1970)). These references utilize the term "microaggregates" to refer to an aggregate having a size in the range of about 1-3 microns. Such microaggregates localize in, and can be used to visualize, the reticuloendothelial system.

The microaggregate products disclosed by Kutas et al., supra, Yamada et al., supra, and Honda et al., supra, are not well suited for commercial use. The references teach the labeling of albumin followed by the subsequent ultrasonication of the labeled aggregates. This type of product is most impractical for large scale distribution. Such a product would require the user to accurately size the particles before administering the product to a patient.

BRIEF DESCRIPTION OF THE INVENTION

It is an object of this invention to provide a product which can be used for the imaging of the reticuloendothelial system.

It is an object of this invention to provide a product useful for the imaging of the reticuloendothelial system which can be supplied in "cold" (unlabeled) form for labeling immediately prior to administration to a patient.

These, and other objects, which will be apparent to the practitioner of this invention, are achieved by the product of this invention. The product of this invention is a composition substantially free of buffer comprising microaggregated particles of denatured albumin having stannous ions bound thereto. Such a composition can be supplied to the user in the form of a suspension or in the form of a lyophilized powder. In either case the user is faced only with the relatively simple and well-known step of labeling the composition with technetium-99m.

This invention is further directed to a unique process for the preparation of aggregates of denatured albumin which can be subjected to ultrasonication to yield microaggregates.

DETAILED DESCRIPTION OF THE INVENTION

Microaggregates of denatured albumin having stannous ions bound thereto can be labeled with technetium-99m and subsequently administered intravenously into a patient for the purpose of imaging the reticuloendothelial system of the patient.

The term "microaggregate," as used throughout the specification, refers to particles having a size in the range of about 0.1 to 3 microns.

The microaggregates of this invention can be prepared by the ultrasonic reduction of macroaggregates of denatured albumin having stannous ions bound thereto. The macroaggregates can be prepared as described in the prior art or according to the novel method of this invention.

Following the method of the prior art for the preparation of macroaggregates the albumin (normal human serum albumin) is first denatured by any art-recognized procedure. One such procedure comprises heating the normal human serum albumin in an aqueous solution of a mineral acid (preferably a dilute solution of hydrochloric acid). The temperature required for denaturation will vary according to the length of heating. Heating the acid solution of albumin at a temperature of about 80° C. for about 30 minutes results in satisfactory denaturation.

Macroaggregated denatured albumin having stannous ions bound thereto can be prepared by first mixing denatured albumin with an aqueous solution of a stannous salt, e.g., stannous fluoride, stannous chloride, stannous sulfate or others, and subsequently adjusting the pH of the solution to within the range of about 4.5 to 5.5 (which encompasses the isoelectric point of the denatured albumin). While the choice of buffer is not critical, either acetate buffer or a combination of acetate and phthalate buffer is preferable.

An alternate, and novel, method for the preparation of macroaggregated denatured albumin having stannous ions bound thereto comprises mixing a dilute acid solution, normal human serum albumin, an aqueous solution of a stannous salt and a buffer, and heating the resulting solution. The advantages of this process will be immediately apparent to the practitioner of this invention. Principally, of course, is the combination of the denaturation step with the rest of the process steps into a single step.

The reagents to be used in the process, i.e., the dilute acid solution, the aqueous solution of a stannous salt, and a buffer, are the same as those used in the prior art process.

The weight ratio of albumin to stannous ion should be of the order of about 5:1 to 20:1, and will preferably be about 7.7:1. The heating of the reagent mixture must be sufficient to denature the albumin (a temperature of about 75°-85° C. is desirable). Heating the mixture to a temperature of about 80° C., cutting off the heat when the 80° C. temperature is reached, and then cooling the mixture to about 25° C. results in satisfactory aggregates.

The particle size of the aggregates of denatured albumin having stannous ions bound thereto, can be adjusted to the desired range of about 0.1 to 3 microns by ultrasonication (preferably utilizing a probe-type ultrasonifier). The resulting particles may be screened through a filter of appropriate mesh size to insure the removal of all particles having a size larger than 3 microns.

In preparing microaggregates of denatured albumin having stannous ions bound thereto, which are to be radiolabeled for scanning of the reticuloendothelial system, it must be insured that the microaggregates do not agglomerate after the ultrasonication step. To this end, it is necessay that prior to ultrasonication, the aggregates of denatured albumin having stannous ions bound thereto be substantially free of buffer. This is accomplished by repeated washings (preferably with water) of the aggregates. To further guard against agglomeration of the microaggregates, an anti-agglomerating agent such as poloxamer 188 may be added to the microaggregate composition.

The microaggregates can be used (after tagging with technetium-99m) in the form prepared above. It is often desirable, however, to store the microaggregates prior to use. If the microaggregates are to be stored, various excipients such as preservatives, surfactants, suspending aids, etc. can be added to the formulation. Dehydrating the formulation (preferably by lyophilization) increases the shell life of the product even further.

The microaggregates of this invention (either in the form of a suspension or in lyophilized form) are tagged with technetium-99m prior to administration to a patient. Sources of technetium-99m are well known in the art. Conveniently, the microaggregates can be mixed with a pertechnetate ($TcO_4$) solution obtained from any one of the commercially available technetium-99m generators (see, for example, the disclosure of U.S. Pat. No. 3,369,121).

The following examples further illustrate the product and process of this invention.

EXAMPLE 1

| Reagents | Amount, ml |
|---|---|
| Human Serum Albumin (HSA), 25% | 25.6 |
| Water for Injection | 1255.0 |
| Hydrochloric Acid, 0.5 N | 45.0 |
| Stannous fluoride (3.6%) | 25.0 |
| Acetate-Phthalate Buffer (0.5 M, 0.25 M) | 250 |

The human serum albumin, water for injection, hydrochloric acid, stannous fluoride solution and the acetate-phthalate buffer are mixed in a reaction kettle. The mixture is heated to 80° C. while being constantly stirred, and cooled to room temperature. The mixture is centrifuged and the supernatant discarded. The aggregates are resuspended in water for injection, the suspension is centrifuged again and the supernatant discarded. The aggregates are resuspended in water for injection and sonicated, at an albumin concentration of 5 mg/ml, using a probe type ultrasonic generator. The resulting microaggregated albumin suspension is refrigerated (about 5° C.).

The preparation is labeled, tested for radiochemical purity and biodistribution in rats as follows. Technetium-99m pertechnetate from a generator is added to 0.5 mg of microaggregated albumin and diluted to 5.0 ml with normal saline. A 0.25 ml aliquot of this preparation is injected into the external jugular vein of each of three rats. After a residence time of 15 minutes the rats are sacrificed, and the organs (liver and lungs) are separated and assayed for radioactivity. The percent of the injected dose is calculated by comparison with appropriate standards.

For testing radiochemical purity, a small sample of the preparation is spotted on a Whatman #3 paper at 3 cm from the bottom and developed immediately by ascending chromatography to approximately 13 cm from the bottom using 85% methanol as the solvent. The strip is removed from the chamber and cut into two parts at a point 6 cm from the bottom. The percent of the radioactivity bound to the aggregates is determined from the formula $$A = (B/C) \times 100$$

where
A = percent activity bound to the aggregates.
B = activity in the origin portion.
C = activity in the total strip (origin + front).

| Microaggregated HSA Suspension | 0.1 | ml |
|---|---|---|
| Tc-99m pertechnetate (from generator) | 0.1 | ml |
| Normal saline (0.9% NaCl) | 4.8 | ml |
| Percent activity bound to aggregates | 99.2 | |
| Percent injected dose in liver | 82.2 | |
| Percent injected dose in lungs | 0.84 | |

EXAMPLE 2

| Reagents | Amount, ml |
|---|---|
| Human Serum Albumin (HSA) 25% | 77 |
| Water for Injection | 2570 |
| Hydrochloric Acid, 0.5 N | 125 |
| Stannous Fluoride, (6.4%) | 50 |
| Acetate-Phthalate Buffer (0.5 M, 0.25 M) | 360 |

The above reagents are mixed in a reaction kettle and heated to 80° C. (±1° C.) while being constantly stirred at the rate of 500 rpm, and immediately cooled to room temperature. The mixture is centrifuged and the supernatant discarded. The aggregates are resuspended in water for injection and the suspension is again centrifuged and the supernatant discarded. The aggregates are resuspended in 2400 ml of water for injection and sonicated using an ultrasonic generator. The sonicated material is diluted with water for injection to give 1.0 mg of albumin per milliliter, filled into vials, and stored at 5° C.

The preparation is labeled and tested following the same procedure set forth in Example 1, except that 0.2 ml of the labeled preparation is injected into rats.

| Microaggregated HSA suspension | 1.0 | ml |
|---|---|---|
| Tc-99m pertechnetate (from generator) | 0.1 | ml |
| Normal saline (0.9% NaCl) | 8.9 | ml |
| Percent injected dose in liver | 86.5 | |
| Percent injected dose in lung | 1.01 | |

EXAMPLE 3

| Reagents | Amount, ml |
|---|---|
| Human Serum Albumin, (HSA) 25% | 64 |
| Water for Injection | 2700 |
| Hydrochloric Acid, 0.5 N | 65 |
| Stannous Fluoride (5.4%) | 50 |
| Acetate-Phthalate Buffer (0.5 M, 0.25 M) | 320 |

The above reagents are mixed in a reaction kettle and heated to 80° C. (±1° C.) while being constantly stirred, and immediately cooled to room temperature. The mixture is centrifuged and the supernatant discarded. The aggregates are resuspended in water for injection, and the suspension is centrifuged again and the supernatant discarded. The aggregates are resuspended in 1600 ml of water for injection and sonicated using a probe type sonifier. The sonicated material is diluted with a solution containing a suspending agent, Poloxamer 188, to yield 1.0 mg of albumin and 10 mg of Poloxamer 188 per milliliter. Vials are filled and the contents lyophilized to dryness. Before the vials are sealed they are flooded with nitrogen. The vials are refrigerated after drying.

A vial containing the lyophilized aggregates is reconstituted with 2.5 ml of water for injection. One ml of the suspension is used in preparing the sample for radiochemical testing and distribution in rats as described in Example 1.

| | | |
|---|---|---|
| Microaggregated HSA suspension | 0.2 | ml |
| Tc-99m pertechnetate (from generator) | 0.1 | ml |
| Normal saline (0.9% NaCl) | 4.7 | ml |
| Percent activity bound to aggregates | 98.7 | |
| Percent injected dose in liver | 88.7 | |
| Percent injected dose in lungs | 0.84 | |

What is claimed is:

1. A composition comprising microaggregated denatured albumin having stannous ions bound thereto, having a particle size in the range of about 0.1 to 3 microns, said composition being substantially free of buffer.

2. A process for preparing aggregates of denatured albumin having stannous ions bound thereto which comprises mixing together normal human serum albumin, a dilute acid solution, an aqueous solution of a stannous salt and a buffer and heating the resulting mixture.

3. A process in accordance with claim 2 wherein the weight ratio of normal human serum albumin to stannous ion is about 5:1 to 20:1.

4. A process in accordance with claim 2 wherein the weight ratio of normal human serum albumin to stannous ion is about 7.7:1.

5. A process in accordance with claim 2 wherein the mixture is heated to a temperature of about 75° C. to 85° C.

6. A process in accordance with claim 2 which further comprises washing the aggregates to remove substantially all of the buffer and adjusting to size of the aggregates to within the range of about 0.1 to 3 microns by ultrasonication.

* * * * *

UNITED STATES PATENT AND TRADEMARK OFFICE
CERTIFICATE OF CORRECTION

PATENT NO. : 4,187,285
DATED : February 5, 1980
INVENTOR(S) : Marion Meeks, et al It is certified that error appears in the above-identified patent and that said Letters Patent are hereby corrected as shown below:

Column 1, line 34, please delete the word "microaggregates" and substitute in its place --microaggregate--

Column 4, Example 2, the table of reagents, please delete "360" and add in its place --380--

Signed and Sealed this

Thirtieth Day of September 1980

[SEAL]

Attest:

SIDNEY A. DIAMOND

Attesting Officer

Commissioner of Patents and Trademarks